US006875427B1

(12) United States Patent
DeVore et al.

(10) Patent No.: US 6,875,427 B1
(45) Date of Patent: Apr. 5, 2005

(54) LIGHT ENERGIZED TISSUE ADHESIVE

(75) Inventors: Dale P. DeVore, Chelmsford, MA (US);
Braden P. DeVore, Westerly, RI (US);
Barbara A. Soltz, Spring Valley, NY (US); Robert Soltz, Spring Valley, NY (US); Michael A. Soltz, Pleasanton, CA (US)

(73) Assignee: Tissue Adhesive Technologies, Inc., Spring Valley, NY (US)

( * ) Notice: Subject to any disclaimer, the term of this patent is extended or adjusted under 35 U.S.C. 154(b) by 137 days.

(21) Appl. No.: 09/973,332

(22) Filed: Oct. 9, 2001

(51) Int. Cl.[7] ............................................... A61K 38/00

(52) U.S. Cl. ...................... 424/78.03; 522/68; 514/526; 128/898

(58) Field of Search ........................ 424/78.03; 522/68; 514/526, 2; 128/898

(56) References Cited

U.S. PATENT DOCUMENTS

| | | | |
|---|---|---|---|
| 5,156,613 A | 10/1992 | Sawyer | |
| 5,164,139 A | 11/1992 | Fujioka et al. | |
| 5,219,895 A | * 6/1993 | Kelman et al. | ............... 522/68 |
| 5,290,552 A | 3/1994 | Sierra et al. | |
| 5,354,336 A | 10/1994 | Kelman et al. | |
| 5,412,076 A | 5/1995 | Gagnieu | |
| 5,552,452 A | 9/1996 | Khadem et al. | |
| 5,618,551 A | 4/1997 | Tardy et al. | |
| 5,690,675 A | 11/1997 | Sawyer et al. | |
| 5,749,895 A | 5/1998 | Sawyer et al. | |
| 5,767,152 A | * 6/1998 | Nielsen et al. | .............. 514/526 |
| 5,791,352 A | 8/1998 | Reich et al. | |
| 5,824,015 A | 10/1998 | Sawyer | |
| 5,874,537 A | 2/1999 | Kelman et al. | |
| 5,895,412 A | 4/1999 | Tucker | |
| 6,136,341 A | 10/2000 | Petito | |
| 6,161,544 A | * 12/2000 | DeVore et al. | .............. 128/898 |
| 6,183,498 B1 | 2/2001 | Devore et al. | |
| 6,197,934 B1 | 3/2001 | DeVore et al. | |
| 6,310,036 B1 | 10/2001 | Browdie | |
| 6,335,007 B1 | 1/2002 | Shimizu et al. | |
| 6,471,993 B1 | 10/2002 | Shastri et al. | |
| 6,495,127 B1 | * 12/2002 | Wallace et al. | .......... 424/78.03 |
| 6,547,794 B2 | 4/2003 | Auge, II | |
| 6,547,806 B1 | 4/2003 | Ding | |
| 2002/0022588 A1 | 2/2002 | Wilkie et al. | |
| 2002/0098222 A1 | 7/2002 | Wironen et al. | |
| 2003/0095993 A1 | 5/2003 | Bentz | |

OTHER PUBLICATIONS

Alberts et al. Molecular biology of the cell. Garland Publishing, Inc. 1994. p. 979, Fig. 19–40.*
Ellis et al. The univerity of minnesota biocatalysis/biodegradation database: microorganism, genomics and prediction. Nucleic Acids Research, 2000, vol. 28, No. 1: 377–379.*

Caroli et al. An experimental study of a cyanocrylate biological adhesive adhesive in view of its use in the fixation of various fractures of the fingers. Ann Chir Main Super 1997; 16(2): 138–45 [Abstract].*

Reece et al., A prospectus on tissue ashesives. The American Journal of Surgery 182 (2001) 40S–44S.*

Guidoin, R, Marceau,D. Coutre, J. Rao, TJ, Merhi, Y. Roy, PE, and De la Fay, D. Collagen coatings as biological sealants for textile arterial prostheses, Biomaterials, 10:642, 1989.

Jakob, H. Campbell, CD, Stemberger, A. Wriedt–Lubbe, I. Blumel, G, and Replogle, RL, Combined application of heterologous collagen and fibrin sealant for liver injuries, J. Surg. Res. 36:571–577, 1984.

Pfab, R. Asherl, R. Erhardt, W. Geissdorfer, K. Stemberger. A. Blumel, G. and Hartung, Animal experiments on hemostasis with collagen–fibrin tissue–adhesive sealant in the nephrostomy tract. Urol. Int. 42: 207–209, 1987.

Jonas, R.A. Ziemer, G. Shoen, FJ, Britton, L. and Castaneda, AR, A new sealent for knitted Dacron prostheses: minimally crosslinked gelatin, J. Vasc. Surg., 7:414–419, 1988.

San–Galli, F, Darrouzet, V, Riverl. J. Baquey, C, Ducassou, D, and Guerin, J. Experimental evaluation of a collagen–coated vicryl mesh as a dural substitute, Neurosurgey, 30:396–401, 1992.

(Continued)

Primary Examiner—Christopher R. Tate
Assistant Examiner—Maury Audet
(74) Attorney, Agent, or Firm—Barlow, Josephs & Holmes, Ltd.

(57) ABSTRACT

Consistent with the present invention, tissue adhesive compositions and an associated laser exposure system are provided for bonding or sealing biological tissues. The compositions are comprised of chemically derivatized soluble collagen which is formulated to concentrations ranging from 300 mg/ml (30%) to 800 mg/ml (80%) collagen protein. In particular, Type I collagen, for example, is first prepared by extraction from bovine or porcine hide and purified. The collagen preparations are then chemically derivatized with sulfhydryl reagents to improve cohesive strength and with secondary derivatizing agents, such as carboxyl groups, to improve the adhesive strength of the solder to the tissue. The compositions are then formed into viscous solutions, gels or solid films, which when exposed to energy generated from an infrared laser, for example, undergo thermally induced phase transitions. Solid or semi-solid protein compositions become less viscous enabling the high concentration protein to penetrate the interstices of treated biological tissue or to fill voids in tissue. As thermal energy is released into the surrounding environment, the protein compositions again become solid or semi-solid, adhering to the treated tissue or tissue space.

21 Claims, 10 Drawing Sheets

OTHER PUBLICATIONS

Goins, KM, Khadem, J, Majmudar, PA, and Ernest, JT, Photodynamic biologic tissue glue to enhance corneal wound healing after radial keratotomy. J. Cataract Refract. Surg., 23: 1331–1338. 1997.

Nakayama, Y and Matsuda T. Photocurable surgical tissue adhesive glues composed of photoreactive gelatin and poly-(ethylene glycol) diacrylate. J. Biomed. Mater. Res., 48:511–521, 1999.

Feito, BA, Rath, AM, Longchampt, E, Azorin, J, Experimental study on the in vivo behavior of a new collagen glue in lung surgery. Eur. j. Cardiothorac. Surg., 17:8–13, 2000.

Czerny, M, Verrel, F, Weber, H, Muller, N, Kircheis, L, Lang, W, Steckmeier, B, and Trubel, W, Collagen patch coated with fibrin glue components. Treatment of suture hole bleedings in vascular reconstruction, J. Cardiovasc. Surg., 41:553–557, 2000.

Sekine, T, Nkamura, T, Shimizu, Y, Ueda, H. Matsumoto, Y, Takimoto, Y, and Kiyotani, T, A new type of surgical adhesive made form procine collagen and polyglutamic acid, J. Biomed. Mater. Res., 54:305–310.

Baar, S, Schorner, C, Rollinghoff, M, Radespiel–Troger, M, Hummer, HP and Carbon, RT, Collagen patches impregnated with antimicrobial agents have a high local antimicrobial efficacy and achieve tissue gluing, Infection, 29:27–31, 2001.

Oiwa, H. Takamoto, S, Murakami, A. Tanaka, O, and Furuse, A, Experimental study of small arterial anastomosis with gelatin–recorcinol–formaldehyde glue and collagen sheet, Artif. Organs 25:281–291, 2001.

Okino, H, Nakayama, Y, Tanaka, M, and Matsuda, T, In situ hydrogelation of photocurable gelatin and drug release, J. Biomed. Mater. Res., 59:233–245, 2002.

Wise, PE, Wudel, LJ, Jr, Belous, AE, Allos, TM, Kuhn, SJ, Fuerer, ID, Washington, MK. Pinson, CW. and Chapman, WC, Biliary reconstruction is enhanced with a collagen–polyethylene gycol sealant, Am. Surg., 68:561–562, 2002.

Martis, G. Miko, I, Szendroi, T. Kathy, S. Kovacs, J. Hajdu, Z, Results with collagen fleece coated with fibrin glue (TachoComb). A macroscopical and histological experiments study, Acta Chir. Hung., 36:221–222, 1997.

Conroy, "Aqueous–based lubricious coating technology: another option for manufactuers," Medical Device Technology, Oct. 1998.

ASI, "U.S. adhesives and sealants market to reach $13.5 billion in 2003," Business New Publishing, Sep. 27, 2000, www.adheisvemag.com/CDA/ArticleInformation/features/BNP_Features?Item/02.101,11471.00.html.

Ellis et al., The university of minnesota biocatalysis/biodegradation database: microorganism. genomics and prediction, Nucleic Acids Research, 2000, vol. 28, No. 1, pp. 377–379.

Alberts et al. Molecular biology of the cell. Garland Publishing, Inc. 1994, pp. 979, Fig. 19–40.

* cited by examiner-

LIGHT ENERGIZED TISSUE ADHESIVE

BACKGROUND OF THE INVENTION

Tissue joining and sealing utilizing sutures and staples is the keystone in modern surgical procedures. An alternative approach utilizes a laser to expose a glue or solder to thereby join adjacent tissues. In many respects, such laser assisted tissue soldering is superior to conventional suture or staple-based methods. The advantages are speed, reduced infection, acceleration in healing, better cosmetic appearance and ease of use particularly in laparoscopic surgery where water tightness and limited access or small size of the repair are important. Laser assisted tissue welding often requires glues or solders for promoting strong bonds, forming a bridge between two apposed tissue sections. The ideal solder is chemically and mechanically matched to the tissue. As a result the solder is strong but stretches and grows with the tissue because of good modulus match. Chromophores mixed with the solder can assist in confining the deposited energy and reduce the impact of tissue imperfections. These additives, however, may be toxic and cause pernicious effects.

The need to provide reliable sutureless closures is paramount to reducing morbidity and mortality rates and lowering health care costs. Achieving complete anastomotic integrity without damaging native tissues will provide the general surgeon with a very powerful tool. For example, laser assisted tissue welding can be used in heart surgery to repair congenital defects thereby eliminating blood loss, the main cause of mortality in these procedures. Tissue welding can also benefit patients with coagulation abnormalities, those suffering from dissection of the aorta and those undergoing minimally invasive coronary artery by-pass grafting (CABG). Laser assisted anastomoses will prevent postoperative leakage in bowel and esophageal repair. It will provide a means for repairing damage to articular cartilage, a common problem affecting joints of millions of people. Sutureless transplantation of osteochondral autografts can reduce pain and recovery time and eventually eliminate the need for total joint replacement. The use of a solder will further reduce dead spaces between circular grafts and provide a bridge for optimizing the different mechanical properties of donor to recipient hyaline cartilage. Laser assisted tissue welding can also be used to repair meniscal and treat osteoartritis and spinal disc injuries and are among other applications of this invention.

Methods reported to date have not gained clinical acceptance. The major reasons include the high level of surgeon skill that is required, the strength, toxicity and resorbability of the tissue solder, the potential for irreparable laser damage and cost of the laser system.

SUMMARY OF THE INVENTION

Consistent with the present invention, a suitable solder and associated laser welding system are provided which avoid the shortcomings of conventional systems described above. For example, the biological solders and sealants consistent with the present invention are biodegradable and do not require chormophores or dyes to promote adhesion. Further, consistent with the present invention, the laser system provides accurate temperature control to eliminate peripheral tissue damage, damage to stay sutures (if required), and large area exposure to reduce treatment time. Further, the use of a feedback controller reduces required surgeon skill. The laser system can be comprised of inexpensive off-the-shelf components and has been designed to be compact, nonintrusive in a surgical setting, inexpensive to manufacture and user friendly.

It is believed that the laser energy disrupts the three-dimensional structure of collagen fibers found in tissues, promoting tissue crosslinking and improving cohesive strength. The films or gels are easy to apply and fix to the tissue surface.

Further consistent with the present invention, a method is provided for preparing suitable protein compositions for use with the laser system. The compositions are comprised of chemically derivatized soluble collagen, which is formulated to concentrations ranging from 300 mg/ml (30%) to 800 mg/ml (80%) collagen protein. In particular, Type I collagen, for example, is first prepared by extraction from animal hide, skin or connective tissue and purified. The collagen preparations are then chemically derivatized with sulfhydryl reagents to improve cohesive strength and with secondary derivatizing agents, such as carboxyl groups, to improve the adhesive strength of the solder to the tissue. The compositions are then formed into liquid, gels or solid films which when exposed to energy generated from an infrared laser, for example, undergo thermally induced phase transitions. Solid or semi-solid protein compositions become less viscous enabling the high concentration protein to penetrate the interstices of treated biological tissue or to fill voids in tissue. As thermal energy is released into the surrounding environment, the protein compositions again become solid or semi-solid, adhering to the treated tissue or tissue space.

In accordance with an additional feature of the present invention, minute quantities of any derivative of commercially available, medical grade cyanoacrylate can be applied to fix and appose tissue edges. Next a layer of the high concentration collagen can be applied adjacent to and on the surface of the tissue to be bonded. This top layer is typically exposed to an infrared laser to melt, denature, and mix the two components to promote both chemical and mechanical bonds to the tissue as well as enhancing intrinsic strength of the composite solder. Infrared laser exposure increases temperature at the bonding site. Feedback control of the laser can be used to adjust solder temperature for optimizing the bonding mechanism to the tissue while preventing thermal damage to adjacent healthy tissue.

It is believed that high concentration collagen compositions described in this invention have an increased volume of linkages to improve the strength performance of the solder while modulating the thermal melt temperatures and solder viscosities. Laser exposure parameters were chosen to rapidly flow the solder and promote physical contact of the solder with the tissue. These parameters include choice of an operating wavelength in the infrared range, power density, pulsed or cw mode, exposure times and tissue temperature. The following examples are illustrative of the invention but are not intended to limit the scope thereof.

BRIEF DESCRIPTION OF THE DRAWINGS

Advantages of the present invention will be apparent from the following detailed description of the presently preferred embodiments thereof, which description should be considered in conjunction with the accompanying drawings in which.

DETAILED DESCRIPTION OF INVENTION

Figure 1:
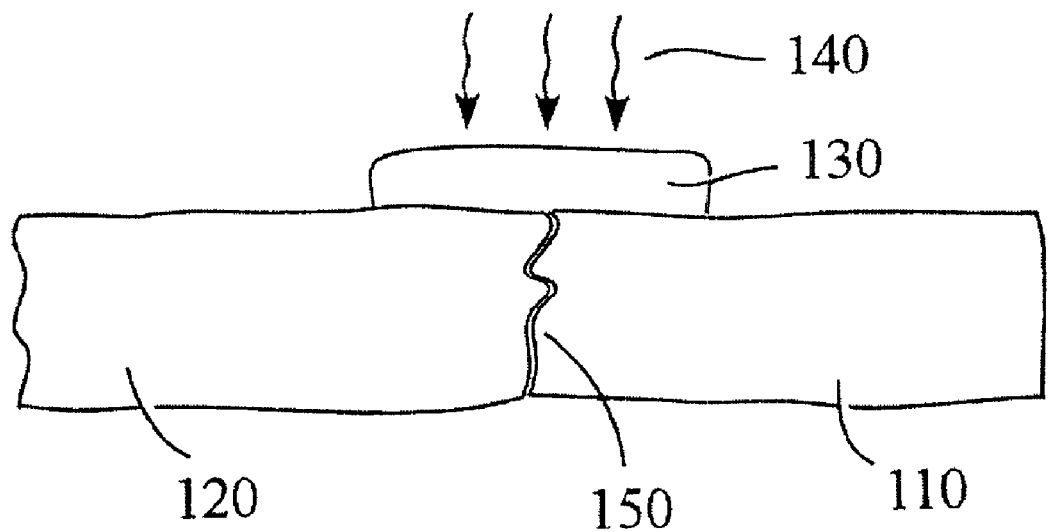
FIG. 1 illustrates an application of a tissue solder, which can be in liquid, gel or solid form, consistent with the present invention to bond two adjacent tissues.

The family of proteins known as collagens are ubiquitous in nature and predominant components of all connective tissues. Type I collagen is the most abundant of the twenty characterized collagens and is commonly used as a biomaterial for medical devices. Collagen-based devices include hemostats, bulking agents, eye shields, punctal plugs, adhesives, drug delivery systems, and others. Collagen is well known to be a biocompatible and safe biomaterial.

Consistent with the present invention, collagen is isolated and purified from various tissue sources including dermis, tendon and ligaments. While collagen is currently prepared from human dermis, most commercial products are prepared using collagen from animal sources. Once a pure form of collagen is prepared, it can be treated in several ways to provide a suitable base protein for use as an adhesive or sealant. These treatments include chemical derivitazation to add functional or reactive groups as well as reduce the pKa of the solder to a more acidic value, and gelatinizing the collagen to create a viscous liquid, gel or solid film having a relatively high protein concentration.

The exemplary solder formulations described herein are suitable for infrared laser activation and include chemically derivatized bovine Type I collagen formed into a liquid, gel or solid film. Collagen was chosen due to its long history as a safe, biocompatible biomaterial and due to its ability to be chemically functionalized into a base formulation with unique cohesive and adhesive characteristics.

1. Exemplary Preparation of Pure Type I Collagen Solutions

Pure, Type I collagen was prepared from calf corium. Corium was cut into small pieces approximately 1 cm$^2$, soaked in reagent alcohol and extensively washed with sterile, deionized water. The washed pieces were then swollen in acetic acid and digested using porcine mucosal pepsin (Sigma Chemical Company, 1:60,000 crystallized and lyophilized). Following 1 or more pepsin treatments, residual pepsin was removed by dialysis and Type I collagen isolated by differential salt precipitation. Purified Type I collagen was dialyzed against acetic acid and filtered through 0.45$\mu$ and 0.22$\mu$ filters. Solder formulations prepared from calf collagen were not successful unless the solutions were extensively dialyzed to remove residual salt (NaCl) and filtered through a 0.22$\mu$ filter. It is believed that 0.22$\mu$ filtration is required to produce monomolecular collagen for subsequent chemical derivatization. Details of pure, soluble Type I bovine collagen are described in U.S. Pat. Nos. 4,713,446; 5,104,957; 5,219,895; 5,476,515; 5,631,243, each of which is incorporated by reference herein. An exemplary collagen purification process is provided below.

a. Skin Preparation:

1) Remove about 25 grams of bovine skin (split calf hide) and cut into small pieces using a scalpel and blade. Wash the skin with sterile, deionized water.

2) Cut the skin into small pieces using a scalpel blade. Weigh pieces and place in a 4 liter beaker containing 3 liters of 0.5M acetic acid. (This is 28.6 ml of concentrated acetic acid per liter or a total of about 86 ml. Add the 86 ml of acetic acid to 3 liters of water).

3) Attach stirrer and stir for 18 hours.

4) Add 2% pepsin to the container. First weigh out 0.5 grams of pepsin and dissolve in 50 ml of deionized water. Then add to the beaker.

5) Continue stirring for 12 hrs. If all of the skin pieces have not dispersed into the acetic acid, add another aliquot of 1% pepsin or 0.25 gram of pepsin powder. Stir for 12 hrs.

6) Filter the suspension through cheesecloth to remove pieces of skin that have not dispersed into the acetic acid. (remove a small sample for analysis-40 ml in a 50 ml centrifuge tube and place in refrigerator.

7) Add solid NaCl (salt) to 0.8 M. This is 140 grams. Add while stirring the collagen solution. Stir for at least two hours to precipitate collagen. Allow the precipitate to settle for 12 hrs.

8) Sipbon-off the clear liquid leaving the collagen precipitate. Then centrifuge the precipitate in centrifuge bottles and collect all the precipitate. Weigh and redissolve in 3 liters of 0.5M acetic acid. (see above for details in preparing the acetic acid solution). Stir for 12 hrs.

9) Take sample of solution, 40 ml in a 50 ml centrifuge tube and cool to 5 C.

10) Again add solid NaCl to 0.8M. Same as above. Stir for at least 2 hrs or until the precipitate is dissolved. Allow precipitate to settle for 12 hrs and centrifuge to collect the pellet. Weigh and redissolve in 0.1 M acetic acid (add 12 ml of acetic acid to 2 liters of deionized water).

11) Stir for 12 hrs to redissolve the collagen. Then dialyze the collagen solution using Spectrapore dialysis tubing, >30,000 molecular weight cut-off. This step will remove dissolved pepsin. Then dialyze against 0.1M acetic acid.

12) Dialyzed volumes will then be filtered through 0.45$\mu$ and then 0.2$\mu$ filters and stored in 1 liter or 4 liter bottles in the refrigerator. This is the collagen stock solution for making collagen-based solder formulations.

2. Chemical Derivatization of Pure Type I Collagen Solution

Derivatization was intended to provide functional groups to enhance both cohesive and adhesive characteristics. For cohesive functionality, thiol groups were attached by derivatization using 4-mercapto-1,8-naphthalic anhydride. Adjacent thiol groups react to form disulfide bonds between collagen molecules enhancing the cohesive properties of this solder. Immediately after derivatization with the 4-mercapto-1,8-naphthalic anhydride, monomolecular collagen is derivatized with glutaric anhydride. This reaction substitutes a $COO^-$ for a $NH_3^+$ making the composition anionic. It is believed that the net negative charge of the solder will ionically interact with positive charged proteins in tissues. This reduces the pKa of collagen to the acidic pH range resulting in a collagen preparation that remains soluble at physiological pH. The derivatization is conducted such that the resultant solder will exhibit a thermal transition at approximately 40–50° C. when exposed to IR laser energy.

To prepare derivatized collagen, adjust 2000 ml collagen solution at 2.5–3.0 mg/ml to pH 8.5–9.5 using 10N and 1N NaOH while stirring at room temperature.

For derivatization to attach both $SH^-$ and $COO^-$ groups, 40 ml of an alcohol saturated solution of mercapto naphthalic anhydride (6 mg/ml) was added to the collagen and mixed for 30 minutes at 2–8° C. and mixed for 15 minutes. Solid glutaric anhydride at 10% collagen weight (600–800 mg of glutaric anhydride) was added and mixed for another 30 minutes at room temperature. The pH was held at pH 8.5–9.5 using 1N NaOH.

At the end of 30 minutes, the solution was centrifuged at 3500 rpm for 10 minutes. The pH of the solution was adjusted to pH 6.8–7.8 as necessary. This solution was lyophilized or air-dried Collagen was also prepared with glutaric anhydride alone or with no derivatization. In the latter case, acid soluble collagen was precipitated at neutral pH and lyophilized or air-dried.

3. Solder Formulations

Solder formulations were prepared from chemically derivatized Type I collagen. Base compositions contained either $COO^-$ functional groups or both $SH^-$ (thiol) and $COO^-$ functional groups. The degree of derivatization with $SH^-$ functional groups was varied in attempts to modulate cohesive characteristics. Remaining free amine groups on the native collagen molecule were derivatized with $COO^-$ groups. Thus, compositions contained approximately the same total net derivatization with $SH^-$ and $COO^-$ groups. The ratio of $SH^-/COO^-$ was intentionally varied. Base preparations contained only $COO^-$ groups. Derivatized collagen solutions were then lyophilized (or air dried and powdered). Lyophilized derivatized collagens were formulated into viscous compositions having from 30–80% collagen solids. Since collagen typically becomes saturated at less than 10% solids, novel techniques were developed to increase total collagen concentrations to 30–80%. This was accomplished by mixing lyophilized or powdered collagen preparations in 0.02M phosphate buffer at pH 6.8–7.8. Mixtures of approximately 50 mg/ml were initially prepared and exposed to thermal energy, in this case microwave energy (output power of 1100 watts, 100% power for 3–5 seconds). Microwave energy generates thermal energy causing the gelatinization of collagen. Other heating methods can be employed such as direct application of a heat source at 50 C, for example. Lyophilized or dried collagen was added to the gelatinized collagen solution and again exposed to microwave energy. This sequence continued until the desired collagen concentration was attained. The final viscous and adhesive formulation was centrifuged at 3500 rpm for 1 minute. The high concentration preparations were then cast into films by pouring hot, centrifuged gelatinized collagen in molds approximately 1 mm thick, and 4 cm square in size. Solidified gelatinized collagen films were sectioned into strips for use with the infrared laser system. An alternate method of preparing films was to gently roll the centrifuge tubes used to deaerate the thick gelatinized collagen formulations. The hot, thick formulation coated the inner surface of the centrifuge tubes in a uniform thickness. Films were removed form the tubes and sectioned into strips for use with the infrared laser system. Increased $SH^-/COO^-$ appeared to increase thermal transition temperature and cohesive characteristics. However, cohesive strength appeared to be only minimal. Attempts to enhance adhesiveness were made by decreasing the $SH^-/COO^-$ ratio. This typically resulted in a reduced thermal transition temperature but with little improvement in adhesive characteristics. It is postulated that a greater increase in anionicity may provide enhanced adhesiveness to tissues.

Additional solder formulations were prepared from collagen derivatized with glutaric anhydride only or from non-derivatized acid soluble collagen. In both cases, it was critical to adjust the gelatinized collagen pH to 6.8–7.8 prior to preparing solder films. Therefore, during the microwave gelatinization and prior to deaeration, the pH was adjusted to 6.8–7.8 by addition of 10N and 1N NaOH. These collagen-based solders appeared to provide the best biomechanical and adhesive characteristics.

FIG. 1 illustrates an exemplary application of the solder or gel and associated laser system consistent with the present invention. First and second tissues 110 and 120 to be joined together, are brought within close proximity with one another. A layer of gelatinized solder 130 to be used as an adhesive is then provided overlying the location where the tissues are to be joined. The solder is then exposed to electromagnetic radiation 140, which in this example, includes infrared light generated by a laser. Upon activation by the laser light, the solder becomes less viscous and therefore flows, for example, into region 150 at the junction of the two tissues 110 and 120. The solder penetrates the interstices of tissues 110 and 120 and fills voids located in region 150. With further application of radiation, the derivatized collagen within the solder crosslinks as well as crosslinking to the underlying tissues. Withdrawing the laser causes the solder to harden and become solid or semi-solid and adhering to the treated areas.

Direct bonding of many tissues can be achieved using the inventive derivatized collagen adhesive alone. Additional adhesive strength, however, can be obtained for bonding some vascular and peritoneal tissues by providing a layer of cyanoacrylate containing material to the tissues prior to application of the derivatized collagen adhesive.

Figure 2:
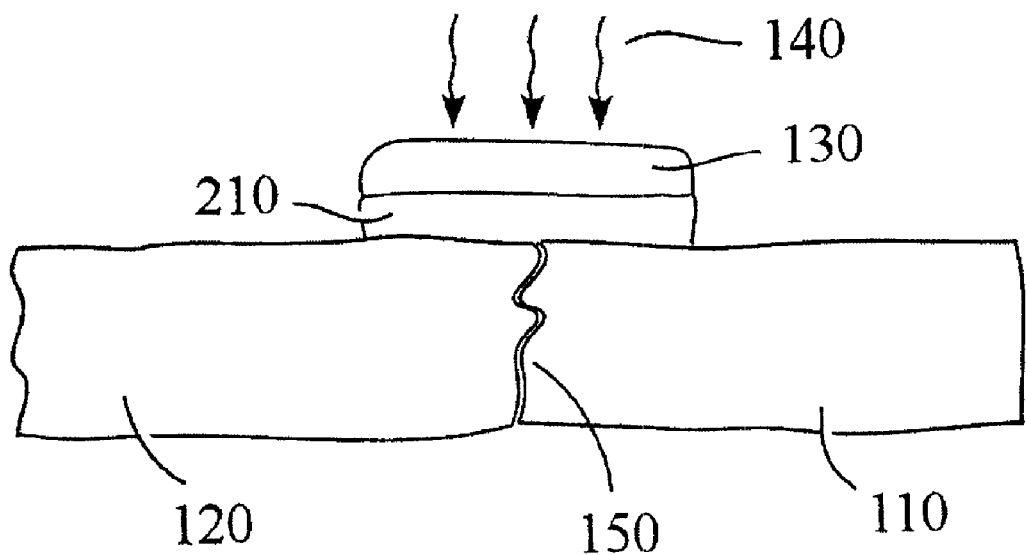
FIG. 2 illustrates an additional application of a tissue solder, which can be in liquid, gel or solid form consistent with the present invention to bond two adjacent tissues.

For example, as shown in FIG. 2, a layer of cyanoacrylate 210 (n-butyl or n-octyl cyanoacrylates, for example) can be initially applied to tissues 110 and 120. The cyanoacrylate layer is believed to interact with $NH_2$ groups in protein molecules in tissues 110 and 120 to initiate nucleophiles, kicking-off monomer polymerization and bonding to protein surfaces. In particular, derivitized collagen formulations, as discussed above, were combined with n-butyl or n-octyl cyanoacrylates, as shown in FIG. 2. The collagen-based solder, and the tissue surface, contain $NH_2$ moieties to initiate polymerization leading to primary chemical bonding with the polymerized cyanoacrylate. This event results in bonding of the solder to the tissue surface. In addition, exposure of the collagen solder to the laser 140 produces enough heat to induce a phase transition of the collagen-based solder from solid or gel to liquid to thereby permit more efficient mixing of the solder with the cyanoacrylate monomer and facilitate penetration of the collagen-based solder into the tissue surface. The former encourages monomer reaction with both the solder and the tissue, and the latter results in some degree of mechanical bonding of the solder with the interacting treated tissue.

Figure 3:
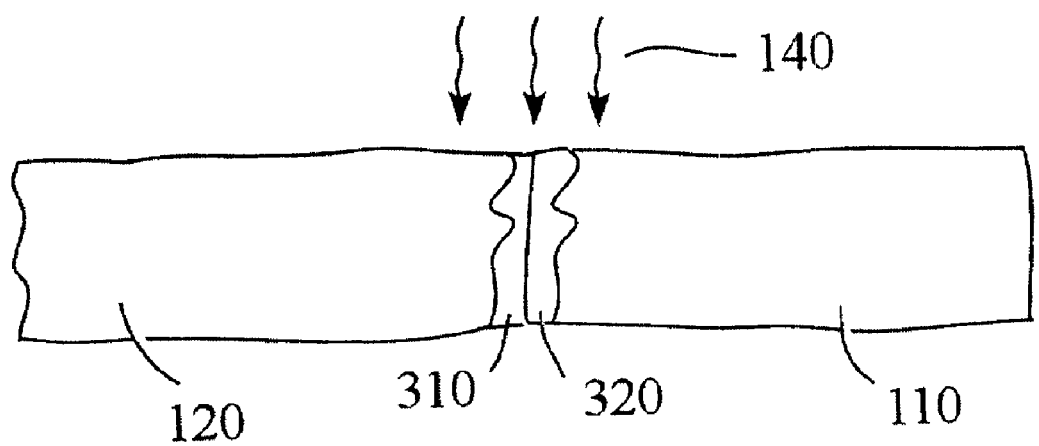
FIG. 3 illustrates an application of a tissue solder, which can be in liquid, gel or solid form consistent with the present invention to bond inner surfaces two adjacent tissues.
Figure 4:
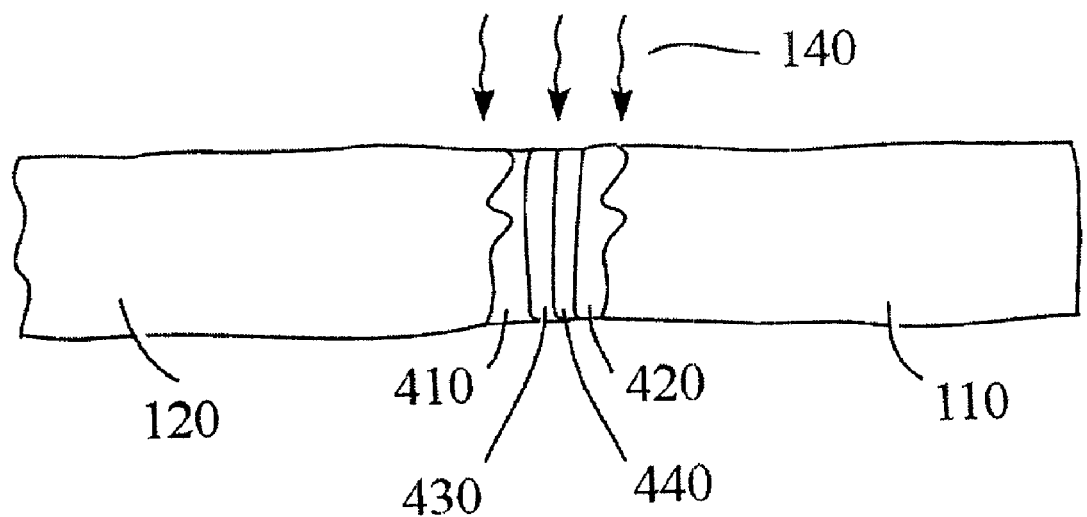
FIG. 4 illustrates an additional application of a tissue solder, which can be in liquid, gel or solid form consistent with the present invention to bond inner surfaces of two adjacent tissues.

Alternative applications are next shown in FIGS. 3 and 4. In FIG. 3, derivatized solder layers 310 and 320 are applied to the inner surfaces of tissues 120 and 110, respectively, and exposed to laser light 140 at the interface between tissues 110 and 120 to complete the welding process. In FIG. 4, cyanoacrylate layers 410 and 420 are applied to inner surfaces of tissues 120 and 110, respectively. Next, derivatized collagen solder layers 430 and 440 are applied to layers 410 and 420, respectively, and exposed to laser light in a manner similar to that described above to thereby facilitate bonding of the two tissue layers.

Figure 5:
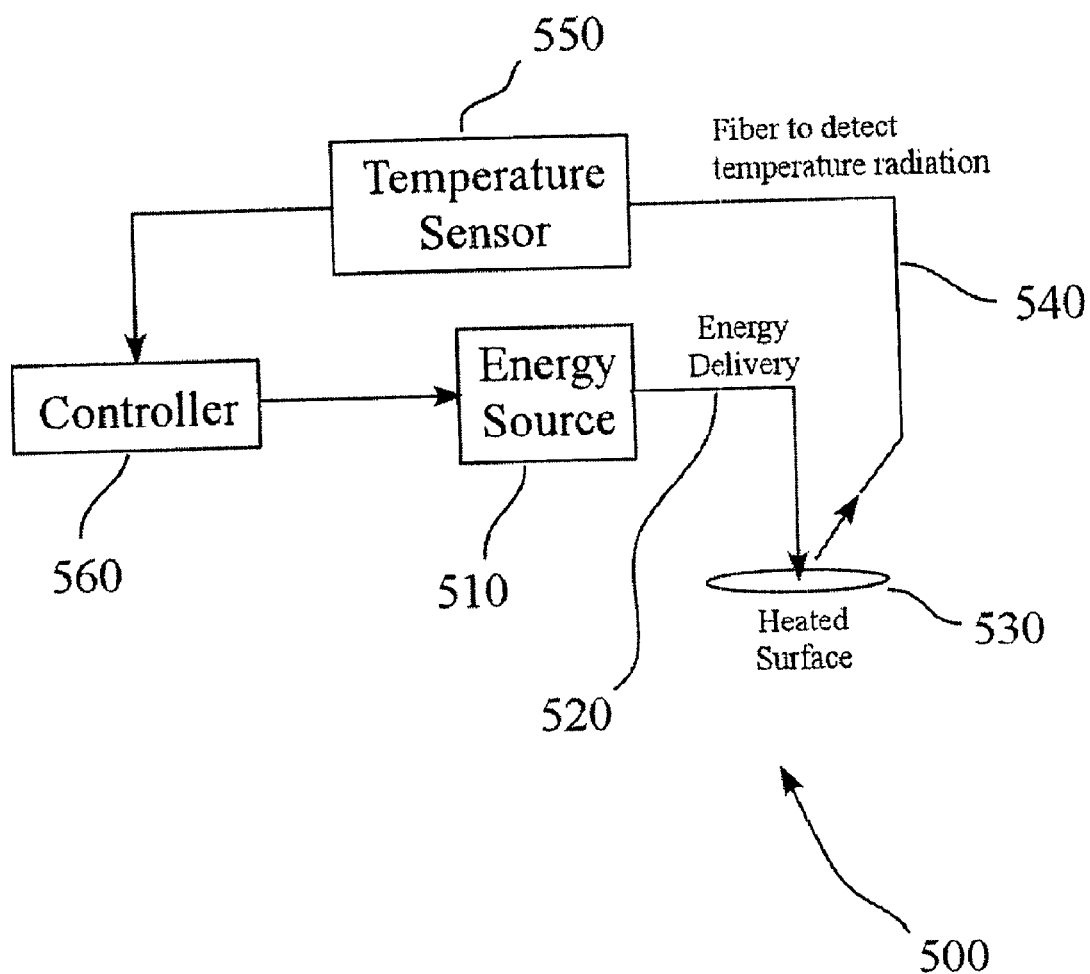
FIG. 5 illustrates a temperature monitoring and laser control system in accordance with a further feature of the present invention.

FIG. 5 illustrates a laser control and monitoring apparatus 500 in accordance with a further feature of the present invention. In apparatus 500, an energy source 510, such as a semiconductor laser emitting light having a wavelength in the infrared range, supplies electromagnetic radiation to a delivery fiber 520. Preferably, the wavelength output from energy source 510 is selected to correspond to an absorption peak of water to thereby effectuate a more efficient coupling of energy from source 510 to target 530 (including the above described solder disposed on a tissue to be joined or bonded together). A second fiber 540 having an end in proximity to the target 530 directs electromagnetic radiation emitted by the target to a temperature sensor circuit 550. The sensed radiation is detected by circuit 550 which generates a sense signal in response to a temperature of the target. Control circuit 560 receives the sense signals and outputs a control signal 510 to thereby adjust an intensity of laser light output from source 510. Thus, the output intensity of source 510 is controlled in accordance with the temperature of target 530.

Examples of tissue welding applications consistent with the present invention will next be described.

EXAMPLE 1

Descending aorta sections were collected from juvenile pigs and stored frozen. Prior to use the tissue, contained in a sealed bag, was thawed 15–20 min in a water bath at room temperature (23° C.). The thawed aorta were cut with a standard single-edged razor blade into 1 cm×1 cm coupons. Excess fascia and loose tissue were removed. The coupons were transferred to a PBS 1× solution that was placed in an ice bath until use.

Figure 10:
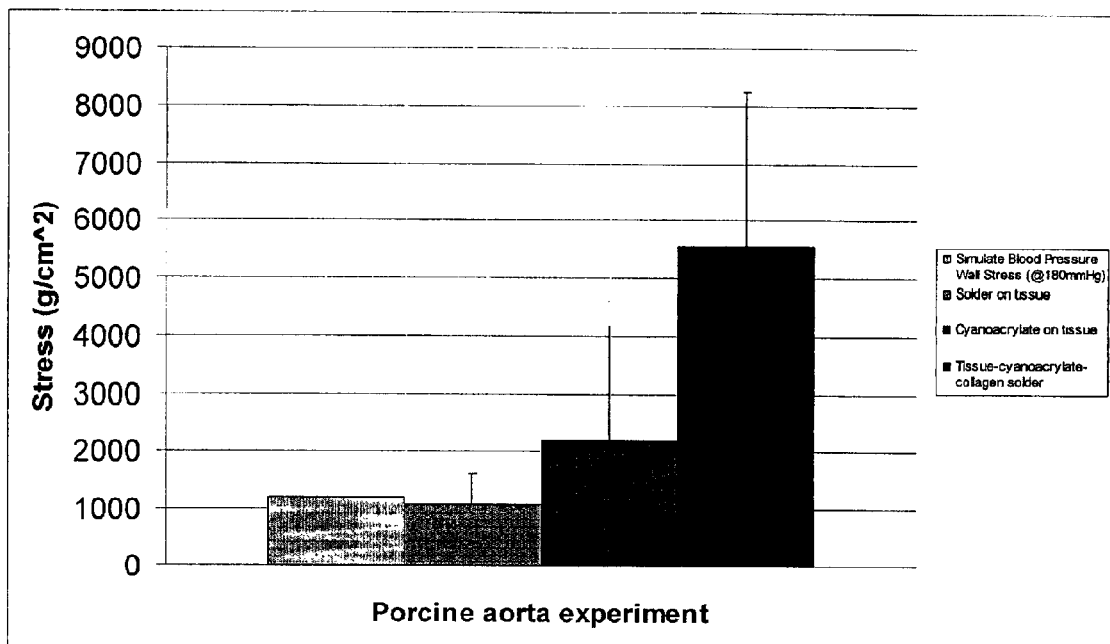
FIG. 10 illustrates a graph of minimum strengths of welded tissues.

The coupons were cut into two 0.5 cm×1 cm pieces and assembled in a butt joint configuration. The incision was first warmed with the laser operating in the 1.4–1.5 micron wavelength range. Laser power density was approximately 10 W/cm2. A minute quantity of medical grade cyanoacrylate is applied sparingly to the apposed tissue edges and thick collagen gels or films were then applied directly to the cut surfaces intended for the joint and subsequently exposed to the laser at a controlled temperature of 55° C. The laser beam was scanned over the entire gel or film for a period of 2–3 min. The gels or films underwent thermal melting. The high concentration fluid covered the incision and penetrated the tissue interstices. Rapid cooling was observed once the laser beam was withdrawn. The melted protein/cyanoacrylate composite became solid and adherent to the tissue providing adequate sealing to prevent fluid leakage. To quantify the welded mechanical strength, tensile tests were performed on coupons of tissue as prepared by the method described above. FIG. 10 summarizes the results. As shown on the first bar of the graph, the minimum strength of the welded tissue was calculated using Laplace's law. An aorta subjected to 180 mmHg blood pressure will achieve a wall stress of 1000 g/cm$^2$. From the experiment, it was found that the combining of the cyanoacrylate and collagen solder had a strength 5 times the minimum required strength. However, the collagen alone or the cyanoacrylate alone achieved a lower maximum strength.

EXAMPLE 2

Several ⅜" diameter articular cartilage plugs were cut with a tubular harvester in the vicinity of bovine carpel joints. The defects were warmed with the laser operating in the 1.4–1.5 micron wavelength range. Laser power density was approximately 10 W/cm2. Thick collagen-based gels were immediately troweled into the defect by a spatula or dispensed with a microsyringe. Care was taken to apply the collagen gel to all surfaces of the implant prior to insertion into the defect. In most cases the implant surfaces were exposed to the laser to liquefy the collagen-based gel then immediately transferred to the defect. The surface temperature was controlled in the 55–60° C. range. After implant placement additional gel was applied and melted with the laser at temperature controlled in the 55–60° C. range. Rapid cooling was observed once the laser beam was withdrawn and the solder formed a solid and adherent seal around the implant. Lift and torque tests were performed immediately following the laser treatment, after 10 min and after overnight storage. Ninety five percent (95%) of the strength was measured immediately following laser exposure with maximum strength observed within 2 hrs.

A collagen-based composition comprised of Type II collagen may be preferred in the treatment of articular cartilage lesions. One method of preparing Type II collagen is described for example in U.S. Pat. No. 5,840,848 incorporated by reference herein.

Although the above described have been discussed for vascular and cartilage type tissues, this invention is applicable for all tissues and wound closures. For other tissues one with ordinary skills would make appropriate modifications to the above described laser operating parameters.

Figure 6:
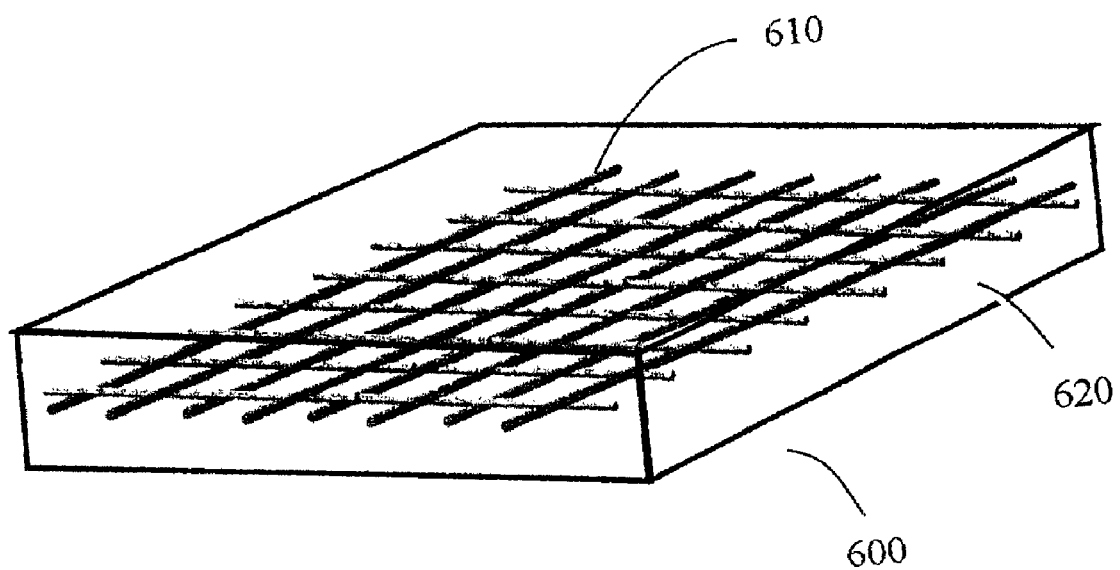
FIG. 6 illustrates an adhesive patch consistent with a further aspect of the present invention.
Figure 8:
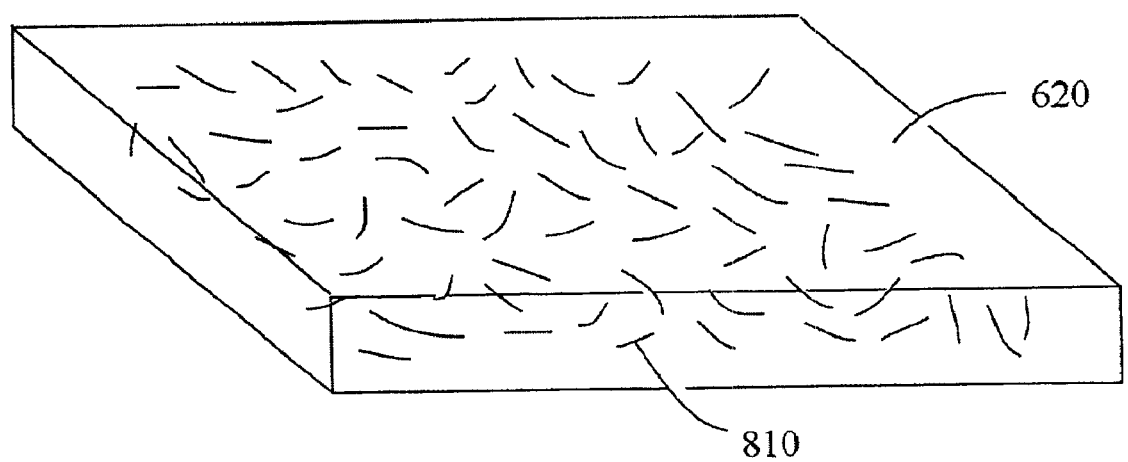
FIGS. 8 and 9 illustrates additional exemplary adhesive patches consistent with the present invention.
Figure 9:
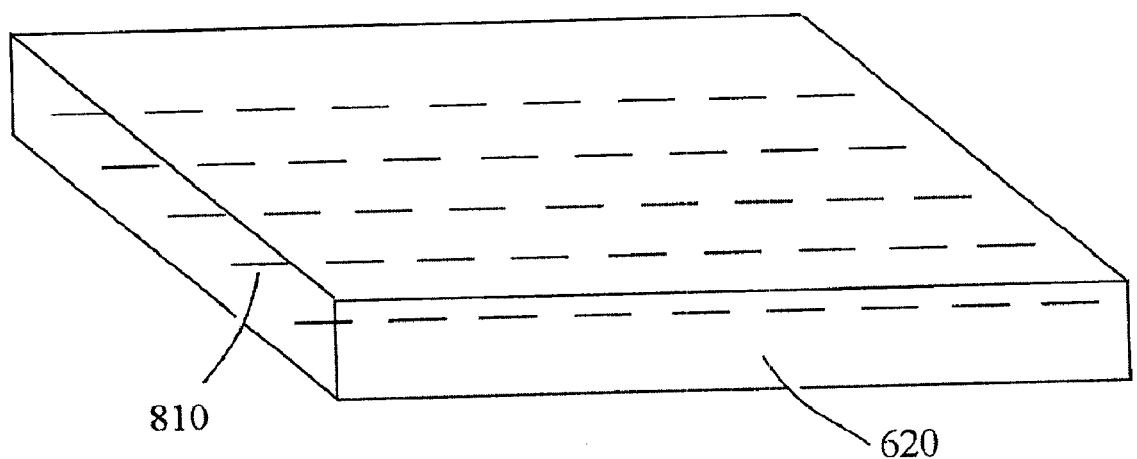

Consistent with a further aspect of the present invention, a tissue adhesive patch 600 can be used to bond tissues instead of layers 130, for example, discussed above. A patch 600 consists of a mesh 610 formed of a polymer (e.g. nylon, polyester or polycarbonate), carbon or metal wire that is biologically compatible and non-irritating. As shown in FIG. 6, the mesh is comprised of a cojoinal network which is encapsulated in a derivatized collagen liquid, gel or solid 620, as discussed above. The mesh can be pre-treated with a combination of etchants, acids or cleaning solutions to enhance the adhesiveness to the base derivatized collagen 620, as discussed above. Patch 600 has increased strength, flexibility or desired electrical characteristics due to the presence of mesh 610. Alternatively, a plurality of fibers 810 (made of biologically compatible and non-irritating material such as a polymer (e.g. nylon, polyester, polycarbonate), carbon or metal can be dispersed throughout layer 620, which can either be oriented randomly (FIG. 8) or coaligned (FIG. 9) to give additional strength, flexibility, uniform heating or electrical properties to the patch 600.

Figure 7:
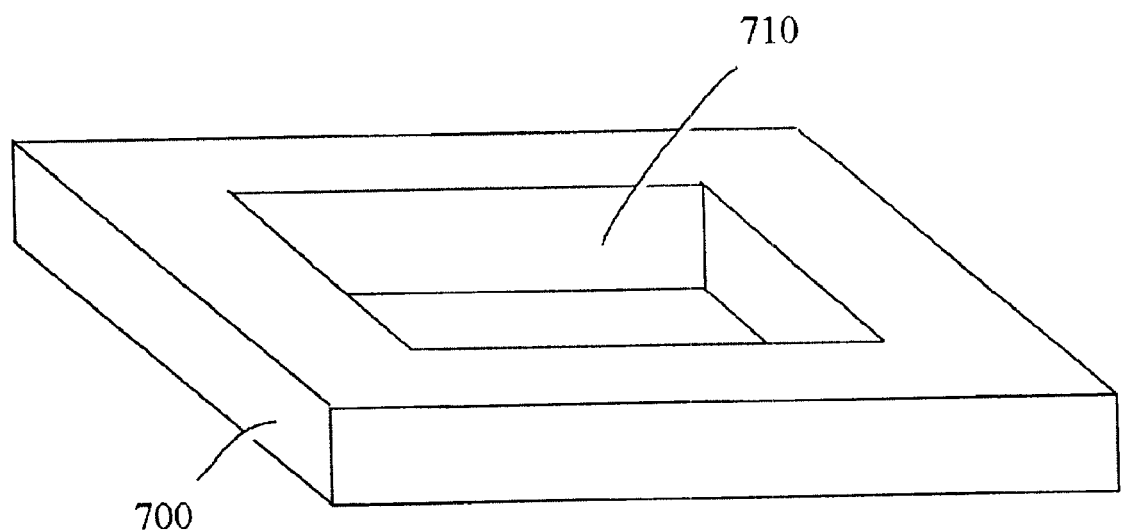
FIG. 7 illustrates a mold used to make the patches shown in FIGS. 6, 8 and 9.

Patch 600 can be formulated by placing a structural element such as fibers 810 or mesh 610 in a recessed portion 710 of mold or template 700, as shown in FIG. 7. Heated derivatized and concentrated collagen, as discussed above, is poured or otherwise supplied to recess 710 and allowed to cool. Patch 600 is then removed from opening 710 and can be exposed to laser light or other electromagnetic radiation to bond or weld tissues in a manner similar to that discussed above. By precisely filling opening 710, patch 600 can be formed with a uniform thickness thereby assuring adequate and uniform bonding of the underlying tissue upon exposure.

Consistent with a further aspect of the present invention, collagen fibrils, fibers, or fiber bundles can be added to the base solder composition to encourage integration of cells and binding of cells from host tissue. Collagen fibrils may be prepared by reconstituting acid soluble or acid soluble-pepsin digested collagen from human or non-human animal sources. Collagen fibrils may be composed predominantly of Type I collagen, Type I collagen/Type III collagen mixtures, Type II collagen, or other collagen Type mixtures. Acid soluble and acid soluble-pepsin digested collagen undergo spontaneous reconstitution (fibrillogenesis) when brought to neutral pH conditions. This can be accomplished by mixing the acid soluble or acid soluble-pepsin digested collagen with appropriate buffer solutions at room temperature or slightly elevated temperatures (up to 40 C) or dialysis against buffer solutions at room temperature or slightly elevated temperatures (up to 40 C) to bring the pH of the acid soluble or acid soluble-pepsin digested collagen to neutral pH. There are many literature publications describing optimal methods for collagen fibril reconstitution. Another method of preparing intact collagen fibrils is described in U.S. Pat. Nos. 4,969,912 and 5,332,802. Such dispersions, predominantly composed of intact collagen fibrils, may be derived from any intact connective tissue including dermis, tendon, ligament, cartilage, or other such collagen containing connective tissue. Any other method of preparing collagen fibrils, collagen fibers, or collagen fiber bundles may also be appropriate.

Collagen fibrils, fibers, or fiber bundles are added to the base solder composition following centrifugation to remove incorporated air (deaeration). The dispersed fibrils, fibers, or fiber bundles are gently mixed with an appropriate mixing tool, i.e., spatula, mixing rod, etc., into the viscous composition avoiding production of air bubbles. If air bubbles are again incorporated, the mixture may be re-centrifuged at lower speed. Higher speeds will result in settling of the fibrils, fiber, or fiber bundles necessitating remixing to form a homogeneous composition. Mixing of fibrils, fibers, or fibril bundles is performed while the high concentration solder is still flowable but at a temperature lower than 65 C and preferably lower than 50 C. Fibril, fiber, or fiber bundle supplemented solder is then cast into films or membranes as described above. Alternately, the composition may be placed in an appropriate delivery system, i.e., syringe or tubular device, such that the solder is able to be delivered by exerting pressure to forcing it through a delivery orifice (caulking gun approach) in a continuous stream.

Collagen fibrils, fibers, or fiber bundles are added to the base solder composition at concentrations (wet weight/volume) ranging from 1%–30%, preferably 5%–20%, and more preferably, 7.5%–15%. Since the addition of intact collagen fibrils, fibers, or fiber bundles increases the total concentration of the solder, it may be necessary to reduce the concentration of the base solder.

It is expected that such fibril, fiber, or fiber bundle solder compositions will encourage host cell integration, cell binding, and cell proliferation.

The invention being thus disclosed and described in connection with the illustrated embodiments, variations and modifications thereof will occur to those skilled in the art, and are intended to be included within the scope of the invention.

What is claimed is:

1. A tissue adhesive, comprising collagen, wherein the concentration of said collagen in said tissue adhesive is 300 mg/ml (30%) up to 800 mg/ml (80%), said collagen being derivatized with a $COO^-$ functional group, and being gelatinized.

2. A tissue adhesive in accordance with claim 1, wherein said collagen is also derivatized with an $SH^-$ functional group.

3. A tissue adhesive in accordance with claim 1, wherein said concentration is within a range of 400 mg/ml up to 800 mg/ml.

4. A tissue adhesive in accordance with claim 1, wherein a pH associated with said tissue adhesive is in a range of 6.8 to 7.8.

5. A tissue adhesive in accordance with claim 1, further comprising an antibacterial agent.

6. A tissue adhesive in accordance with claim 1, further comprising water.

7. A tissue adhesive in accordance with claim 1, wherein said composition is biodegradable.

8. A tissue adhesive in accordance with claim 1, further comprising material selected from the group of collagen fibrils, fibers or fiber bundles.

9. A tissue adhesive in accordance with claim 8, wherein a concentration of said material is within a range of 1%–30%.

10. A tissue adhesive in accordance with claim 1, wherein said tissue adhesive is a gel.

11. A tissue adhesive in accordance with claim 1, wherein said tissue adhesive is a liquid.

12. A tissue adhesive comprising derivatized collagen, wherein the concentration of said derivatized collagen in said tissue adhesive is 300 mg/ml (30%) up to 800 mg/ml (80%), said derivatized collagen being derivatized with $COO^-$ and $SH^-$ functional groups, and said derivatized collagen being gelatinized.

13. A tissue adhesive in accordance with claim 12, wherein said concentration is within a range of 400 mg/ml up to 800 mg/ml.

14. A tissue adhesive in accordance with claim 12, wherein a pH associated with said tissue adhesive is in a range of 6.8 to 7.8.

15. A tissue adhesive in accordance with claim 12, further comprising an antibacterial agent.

16. A tissue adhesive in accordance with claim 12, further comprising water.

17. A tissue adhesive in accordance with claim 12, wherein said tissue adhesive is biodegradable.

18. A tissue adhesive in accordance with claim 12, further comprising material selected from the group of collagen fibrils, fibers or fiber bundles.

19. A tissue adhesive in accordance with claim 18, wherein a concentration of said material is within a range of 1% to 30%.

20. A tissue adhesive in accordance with claim 12, wherein said composition is a gel.

21. A tissue adhesive in accordance with claim 12, wherein said composition is a liquid.

* * * * *